(12) United States Patent
Zhao et al.

(10) Patent No.: US 8,182,426 B2
(45) Date of Patent: May 22, 2012

(54) DOCKING STATION AND ULTRASONIC DIAGNOSTIC SYSTEM

(75) Inventors: Zhensong Zhao, Wuxi (CN); Lanping Liu, Wuxi (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 371 days.

(21) Appl. No.: 12/431,542

(22) Filed: Apr. 28, 2009

(65) Prior Publication Data
US 2009/0270727 A1    Oct. 29, 2009

(30) Foreign Application Priority Data
Apr. 29, 2008   (CN) .......................... 2008 1 0083966

(51) Int. Cl.
*A61B 8/00* (2006.01)
*G06F 1/16* (2006.01)

(52) U.S. Cl. ............... 600/437; 600/459; 361/679.21; 361/679.41

(58) Field of Classification Search ............ 600/437, 600/439, 459; 361/679.21, 679.27, 679.4, 361/679.41, 679.42, 679.43, 679.44; 248/146, 248/917; 710/303; 348/836, 843
See application file for complete search history.

(56) References Cited

U.S. PATENT DOCUMENTS

| | | | |
|---|---|---|---|
| 5,375,604 A | 12/1994 | Kelly et al. | |
| 5,436,792 A | 7/1995 | Leman et al. | |
| 5,500,982 A * | 3/1996 | Hosoi | 16/297 |
| 5,555,491 A | 9/1996 | Tao | |
| 5,685,314 A | 11/1997 | Geheb et al. | |
| 5,745,341 A | 4/1998 | Wolff et al. | |
| 5,838,539 A | 11/1998 | Doss et al. | |
| 5,859,762 A | 1/1999 | Clark et al. | |
| 5,899,421 A | 5/1999 | Silverman | |
| 5,915,661 A | 6/1999 | Silverman et al. | |
| 6,016,171 A * | 1/2000 | Tsao | 361/679.27 |
| 6,102,284 A * | 8/2000 | Myers et al. | 235/375 |
| 6,183,417 B1 | 2/2001 | Geheb et al. | |
| 6,185,095 B1 | 2/2001 | Helot et al. | |
| 6,216,195 B1 | 4/2001 | Lee et al. | |
| 6,222,728 B1 | 4/2001 | Jaggers et al. | |
| 6,594,146 B2 | 7/2003 | Frangesch et al. | |
| 6,608,749 B2 * | 8/2003 | Hubbard | 361/679.09 |
| 6,856,506 B2 | 2/2005 | Doherty et al. | |
| 7,009,840 B2 | 3/2006 | Clark et al. | |
| 7,052,296 B2 | 5/2006 | Yang et al. | |
| 7,274,564 B2 * | 9/2007 | Rossini | 361/679.41 |

OTHER PUBLICATIONS

Nowatschin et al. "A system for analyzing intraoperative B-Mode ultrasound scans of the liver," Engineering in Medicine and Biology Society, 2007. EMBS 2007. 29th Annual International Conference of the IEEE, vol., No., pp. 1346-1349, Aug. 22-26, 2007. doi: 10.1109/IEMBS.2007.4352547.*

* cited by examiner

*Primary Examiner* — Brian Casler
*Assistant Examiner* — Phong K Huynh
(74) *Attorney, Agent, or Firm* — Armstrong Teasdale LLP

(57) ABSTRACT

An ultrasonic diagnostic system has a tablet type electronic device for ultrasonic diagnosis and a docking station for mounting thereto the electronic device removably. The docking station includes a receptacle section against which one side of the electronic device comes into abutment when mounting the electronic device, and a hold-down section for holding down the electronic device releasably on the side opposite to the one side when mounting the electronic device.

14 Claims, 14 Drawing Sheets

DOCKING STATION AND ULTRASONIC DIAGNOSTIC SYSTEM

CROSS REFERENCE TO RELATED APPLICATIONS

This application claims the benefit of Chinese Patent Application No. 200810083966.0 filed Apr. 29, 2008, which is hereby incorporated by reference in its entirety.

BACKGROUND OF THE INVENTION

The present invention relates to a docking station and an ultrasonic diagnostic system. More particularly, the embodiments described herein are concerned with a docking station for mounting thereto a tablet type electronic device removably and an ultrasonic diagnostic system equipped with such a docking station.

The tablet type electronic device is superior in mobility and is therefore bought in and used by users in various fields. The application field of the tablet type electronic device covers various fields, including, for example, manufacture, construction, agriculture and fisheries, distribution, financing, science and medical care.

The function of the tablet type electronic device is limited, so when extension of the function is needed, the electronic device is docked to an extension station and a required extension device is connected to a port of the extension station at a nearby base or a home office.

The extension device connected to the docking station is a dedicated device such as a general-purpose device, e.g., display, keyboard, HDD (hard disk drive), DVD recorder (digital versatile disk recorder), printer, or modem, or a power supply for charging.

The extension station is also called a docking station. The docking station uses a docking assembly to hold the tablet type electronic device. With use of a holding mechanism of a rack-like structure, the docking assembly holds the bottom and both sides of the tablet type electronic device. The holding mechanism has a connector for electrical connection at its portion against which the bottom of the tablet type electronic device comes into abutment (see, for example, U.S. Pat. No. 6,856,506).

In the docking station referred to above, the mounting and removal of the tablet type electronic device are easy, but when the docking station is carried on a cart or a vehicle, there arises the problem that the state of docking with the tablet type electronic device is apt to become loose under the influence of vibration or shock during travel.

BRIEF DESCRIPTION OF THE INVENTION

In a first aspect of the invention there is provided a docking station for mounting thereto a tablet type electronic device removably, the docking station including a receptacle section against which one side of the electronic device comes into abutment when mounting the electronic device and a hold-down section for holding down the electronic device releasably on the side opposite to the one side when mounting the electronic device.

In a second aspect of the invention there is provided, in combination with the above first aspect, a docking station wherein the hold-down section includes a hold-down member for holding down the opposite side of the electronic device, a support mechanism for supporting the hold-down member so that the hold-down member is movable between a hold-down position and a release position and pivotable in a direction away from the electronic device at the release position, a locking mechanism for locking the hold-down member releasably at the hold-down position, and an urging member for urging the hold-down member from the hold-down position toward the release position.

In a third aspect of the invention there is provided, in combination with the above second aspect, a docking station wherein the hold-down member includes a curved portion adapted to cover the opposite side of the electronic device when holding down the electronic device, a flat plate portion extending from a base portion of the curved portion, a cam slot formed in the flat plate portion, and a shaft of an elliptic section provided at an end in the extending direction of the flat plate portion perpendicularly to the extending direction and in parallel with the plate surface.

In a fourth aspect of the invention there is provided, in combination with the above third aspect, a docking station wherein the support mechanism includes a support member for supporting the shaft of the hold-down member so that the shaft is movable in parallel between the hold-down position and the release position and rotatable at the release position.

In a fifth aspect of the invention there is provided, in combination with the above fourth aspect, a docking station wherein the support member includes a guide slot, the guide slot having a width conforming to a minor diameter of the elliptic section of the shaft and also having a length corresponding to the distance between the hold-down position and the release position, and a bearing hole formed in an end of the release position side of the guide slot and having an inside diameter conforming to a major diameter of the elliptic section of the shaft.

In a sixth aspect of the invention there is provided, in combination with the above third aspect, a docking station wherein the locking mechanism includes a pin adapted to engage the cam slot of the hold-down member to lock the hold-down member in the hold-down position, a link adapted to be operated manually to cause the pin to move along the cam slot, thereby releasing the hold-down member locked by the pin, and an urging member for urging the link in a direction opposite to the direction of the manual operation.

In a seventh aspect of the invention there is provided, in combination with the above sixth aspect, a docking station wherein the urging member is a coil spring.

In an eighth aspect of the invention there is provided, in combination with the above first aspect, a docking station wherein the hold-down section holds down the electronic device in a direction to push the electronic device against the receptacle section.

In a ninth aspect of the invention there is provided, in combination with the above first aspect, a docking station wherein the receptacle section has an electrical connector.

In a tenth aspect of the invention there is provided, in combination with the above first aspect, a docking station wherein the receptacle section receives therein the electronic device in an upright state.

In an eleventh aspect of the invention there is provided an ultrasonic diagnostic system having a tablet type electronic device for ultrasonic diagnosis and a docking station for mounting thereto the electronic device removably, the docking station including a receptacle section against which one side of the electronic device comes into abutment when mounting the electronic device and a hold-down section for holding down the electronic device releasably on the side opposite to the one side when mounting the electronic device.

In a twelfth aspect of the invention there is provided, in combination with the above eleventh aspect, an ultrasonic diagnostic system wherein the hold-down section includes a hold-down member for holding down the opposite side of the electronic device, a support mechanism for supporting the hold-down member so that the hold-down member is movable between a hold-down position and a release position and pivotable in a direction away from the electronic device at the release position, a locking mechanism for locking the hold-down member releasably at the hold-down position, and an urging member for urging the hold-down member from the hold-down position toward the release position.

In a thirteenth aspect of the invention there is provided, in combination with the above twelfth aspect, an ultrasonic diagnostic system wherein the hold-down member includes a curved portion adapted to cover the opposite side of the electronic device when holding down the electronic device, a flat plate portion extending from a base portion of the curved portion, a cam slot formed in the flat plate portion, and a shaft of an elliptic section provided at an end in the extending direction of the flat plate portion perpendicularly to the extending direction and in parallel with the plate surface.

In a fourteenth aspect of the invention there is provided, in combination with the above thirteenth aspect, an ultrasonic diagnostic system wherein the support mechanism includes a support member for supporting the shaft of the hold-down member so that the shaft is movable in parallel between the hold-down position and the release position and rotatable at the release position.

In a fifteenth aspect of the invention there is provided, in combination with the above fourteenth aspect, an ultrasonic diagnostic system wherein the support member includes a guide slot, the guide slot having a width conforming to a minor diameter of the elliptic section of the shaft and also having a length corresponding to the distance between the hold-down position and the release position, and a bearing hole formed in an end of the release position side of the guide slot and having an inside diameter conforming to a major diameter of the elliptic section of the shaft.

In a sixteenth aspect of the invention there is provided, in combination with the above thirteenth aspect, an ultrasonic diagnostic system wherein the locking mechanism includes a pin adapted to engage the cam slot of the hold-down member to lock the hold-down member in the hold-down position, a link adapted to be operated manually to cause the pin to move along the cam slot, thereby releasing the hold-down member locked by the pin, and an urging member for urging the link in a direction opposite to the direction of the manual operation.

In a seventeenth aspect of the invention there is provided, in combination with the above twelfth or sixteenth aspect, an ultrasonic diagnostic system wherein the urging member is a coil spring.

In an eighteenth aspect of the invention there is provided, in combination with the above eleventh aspect, an ultrasonic diagnostic system wherein the hold-down section holds down the electronic device in a direction to push the electronic device against the receptacle section.

In a nineteenth aspect of the invention there is provided, in combination with the above eleventh aspect, an ultrasonic diagnostic system wherein the receptacle section has an electrical connector.

In a twentieth aspect of the invention there is provided, in combination with the above eleventh aspect, an ultrasonic diagnostic system wherein the receptacle section receives therein the electronic device in an upright state.

The docking station according to the first aspect of the invention, which is for mounting thereto a tablet type electronic device removably, includes a receptacle section against which one side of the electronic device comes into abutment when mounting the electronic device and a hold-down section for holding down the electronic device releasably on the side opposite to the one side when mounting the electronic device. Therefore, it is possible to provide a docking station that permits easy mounting and removal of the tablet type electronic device and which is superior in docking stability.

According to the eleventh aspect of the invention, in an ultrasonic diagnostic system having a tablet type electronic device for ultrasonic diagnosis and a docking station for mounting thereto the electronic device removably, the docking station includes a receptacle section against which one side of the electronic device comes into abutment when mounting the electronic device and a hold-down section for holding down the electronic device releasably on the side opposite to the one side when mounting the electronic device. Therefore, it is possible to provide an ultrasonic diagnostic system equipped with a docking station that permits easy mounting and removal of the tablet type electronic device and which is superior in docking stability.

According to the second or twelfth aspect of the invention, the hold-down section includes a hold-down member for holding down the opposite side of the electronic device, a support mechanism for supporting the hold-down member so that the hold-down member is movable between a hold-down position and a release position and pivotable in a direction away from the electronic device at the release position, a locking mechanism for locking the hold-down member releasably at the hold-down position, and an urging member for urging the hold-down member from the hold-down position toward the release position. Thus, the electronic device can be mounted and removed by simple operations.

According to the third or thirteenth aspect of the invention, the hold-down member includes a curved portion adapted to cover the opposite side of the electronic device when holding down the electronic device, a flat plate portion extending from a base portion of the curved portion, a cam slot formed in the flat plate portion, and a shaft of an elliptic section provided at an end in the extending direction of the flat plate portion perpendicularly to the extending direction and in parallel with the plate surface. Thus, the construction of the hold-down member can be simplified.

According to the fourth or fourteenth aspect of the invention, the support mechanism includes a support member for supporting the shaft of the hold-down member so that the shaft is movable in parallel between the hold-down position and the release position and rotatable at the release position. Therefore, the electronic device can be easily held down by the hold-down member and released.

According to the fifth or fifteenth aspect of the invention, the support member includes a guide slot, the guide slot having a width conforming to a minor diameter of the elliptic section of the shaft and also having a length corresponding to the distance between the hold-down position and the release position, and a bearing hole formed in an end of the release position side of the guide slot and having an inside diameter conforming to a major diameter of the elliptic section of the shaft. Therefore, the construction of the support mechanism can be simplified.

According to the sixth or sixteenth aspect of the invention, the locking mechanism includes a pin adapted to engage the cam slot of the hold-down member to lock the hold-down member in the hold-down position, a link adapted to be operated manually to cause the pin to move along the cam slot, thereby releasing the hold-down member locked by the pin, and an urging member for urging the link in a direction opposite to the direction of the manual operation. Thus, the construction of the locking mechanism can be simplified.

According to the seventh or seventeenth aspect of the invention, since the urging member is a coil spring, it is possible to simplify the construction of the urging member.

According to the eighth or eighteenth aspect of the invention, since the hold-down section holds down the electronic device in a direction to push the electronic device against the receptacle section, it is possible to enhance the docking stability.

According to the ninth or nineteenth aspect of the invention, since the receptacle section has an electrical connector, it is possible to form an electrical connection with the electronic device.

According to the tenth or twentieth aspect of the invention, since the receptacle section receives therein the electronic device in an upright state, it is easy to observe the tablet surface of the electronic device.

Further objects and advantages of the invention will be apparent from the following description of the preferred embodiments of the invention as illustrated in the accompanying drawings.

DETAILED DESCRIPTION OF THE INVENTION

Embodiments of the invention will be described below with reference to the drawings, provided the invention is not limited to the embodiments described herein.

Figure 1:
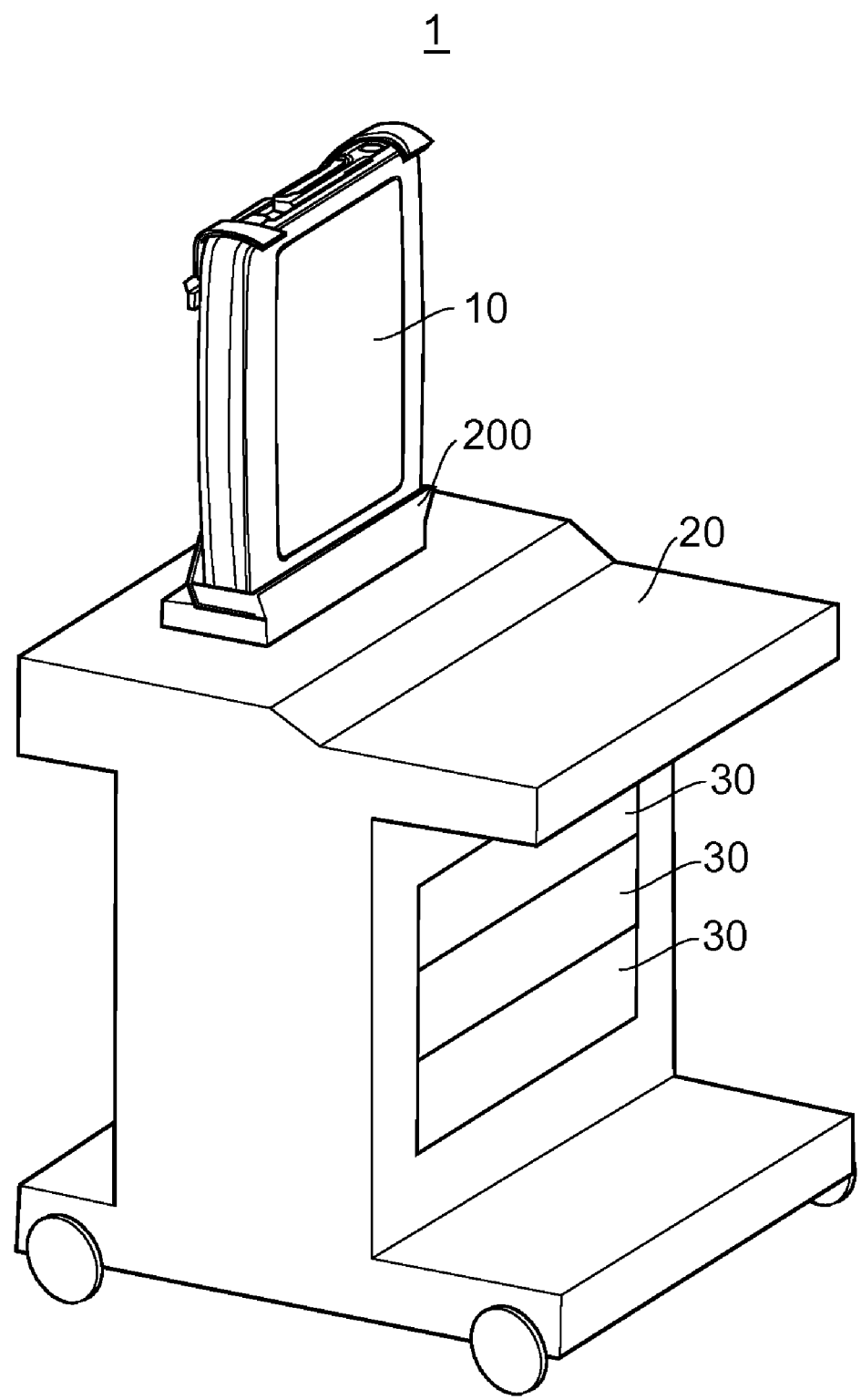
FIG. 1 illustrates the construction of an exemplary ultrasonic diagnostic system.

FIG. 1 illustrates the construction of an exemplary ultrasonic diagnostic system 1 schematically. The ultrasonic diagnostic system 1 is an example of the best mode for carrying out the invention. By the construction of the ultrasonic diagnostic system 1 there is shown an example of the best mode for carrying out the invention with respect to the ultrasonic diagnostic system.

As shown in FIG. 1, the ultrasonic diagnostic system 1 is constituted by a coupling of three types of electronic devices 10, 20 and 30. The electronic device 10 is a tablet type electronic device for ultrasonic diagnosis. The electronic device 10 has an appearance similar to that of a tablet type hand held computer. The electronic device 10 will hereinafter be referred to also as an ultrasonic diagnostic device 10. The ultrasonic diagnostic device 10 is an example of the tablet type electronic device for ultrasonic diagnosis in the invention.

The electronic device 20 is a docking station. The electronic device 20 is equipped with various electronics systems for functional extension of the ultrasonic diagnostic device 10 such as, for example, function-strengthened probe drive system, keyboard system, data processing system, memory system, power supply system, and peripheral device connection system. The electronic device 20 has traveling wheels and functions also as a cart. The electronic device 20 will hereinafter be referred to also as a docking station 20. The docking station 20 is an example of the docking station in the invention.

The docking station 20 is also an example of the best mode for carrying out the invention. By the construction of the docking station 20 there is shown an example of the best mode for carrying out the invention with respect to the docking station.

The electronic device 30 is a peripheral device. As peripheral devices there are used, for example, mass storage devices, e.g., HDD, image storage devices, e.g., DVD recorder and VCR (video cassette recorder), printers, e.g., monochrome printer and color printer, and other suitable general-purpose devices. The electronic device 30 will hereinafter be referred to also as a peripheral device 30.

The electronic device 10 is not limited to the ultrasonic diagnostic device, but may be a suitable tablet type electronic device. The electronic devices 20 and 30 are not limited to the docking station and peripheral device for ultrasonic diagnostic devices, but may be docking station and peripheral device for functional extension of the electronic device 10 concerned. The traveling wheels are not always essential.

The ultrasonic diagnostic device 10 is mounted on top of the docking station 20. The docking station 20 is provided on its top with a docking assembly 200. The ultrasonic diagnostic device 10 is held in an upright state by the docking assembly 200 so that the tablet face thereof becomes a front face.

The docking assembly 200 may be one that holds the ultrasonic diagnostic device 10 in any other attitude than the upright attitude. More particularly, it may be one that holds the ultrasonic diagnostic device 10 in any other suitable attitude, for example, in an inclined state or in a horizontal state.

The ultrasonic diagnostic device 10 and the docking station 20 are rendered integral with each other mechanically and electrically. The peripheral device 30 is accommodated within a tray disposed in a lower portion of the docking station 20 and is connected to the docking station 20 through a signal cable.

The ultrasonic diagnostic device 10 combines with the docking station 20 to constitute an ultrasonic diagnostic system of full equipment. The ultrasonic diagnostic device 10 is removable from the docking station 20 and can independently perform a basic ultrasonic diagnosis. In this case, the ultrasonic diagnostic device 10 operates with electric power of a built-in battery.

Figure 2:
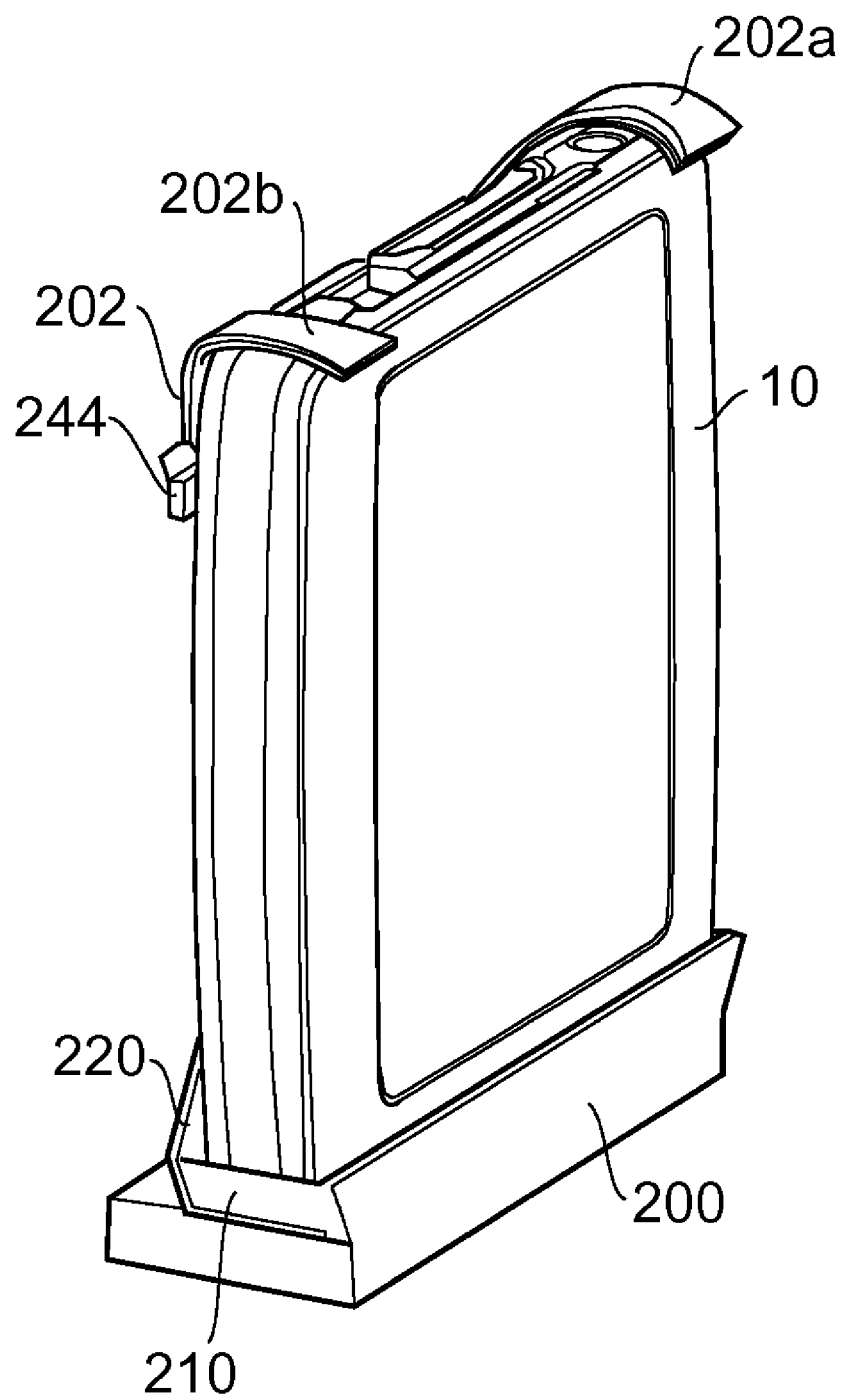
FIG. 2 illustrates in what state an ultrasonic diagnostic device is held by a docking assembly.

FIG. 2 illustrates in what state the ultrasonic diagnostic device 10 is held by the docking assembly 200. As shown in FIG. 2, a bottom side of the ultrasonic diagnostic device 10 comes into abutment from above against a receptacle section 210 of the docking assembly 200 and an upper side thereof is held down from above by a hold-down member 202.

As a result, the ultrasonic diagnostic device 10 and the docking station 20 are docked together firmly and there is no fear of this docked state being loosened or released even with vibration or shock applied from the exterior. That is, docking stability is ensured.

The receptacle section 210 is an example of the receptacle section in the invention. The hold-down member 202 is an example of a part of the hold-down section in the invention. The bottom side of the ultrasonic diagnostic device is an example of one side of the electronic device in the invention and the upper side thereof is an example of the side opposite to the one side of the electronic device in the invention.

The hold-down member 202 is supported by a support mechanism attached to a back plate 220 and to be described later.

The back plate 220 rises from the receptacle section 210 along the back side of the ultrasonic diagnostic device 10 and a lower end portion thereof is fixed to the receptacle section 210.

The hold-down member 202 is a plate having two hook-like curved portions 202a and 202b. The curved portions 202a and 202b cover two right and left upper-side portions of the ultrasonic diagnostic device 10 and hold down the ultrasonic diagnostic device 10 in a direction to push the device 10 against the receptacle section 210. The curved portions 202a and 202b are an example of the curved portion in the invention.

The hold-down member 202, in its holding-down condition, is locked by a locking mechanism to be described later. The locking mechanism can be released by operating the slide link 244 manually. Upon unlocking, the hold-down member 202 moves upward from the hold-down position to release the upper side of the ultrasonic diagnostic device 10. At the release position the hold-down member 202 can pivot backward.

Figure 3:
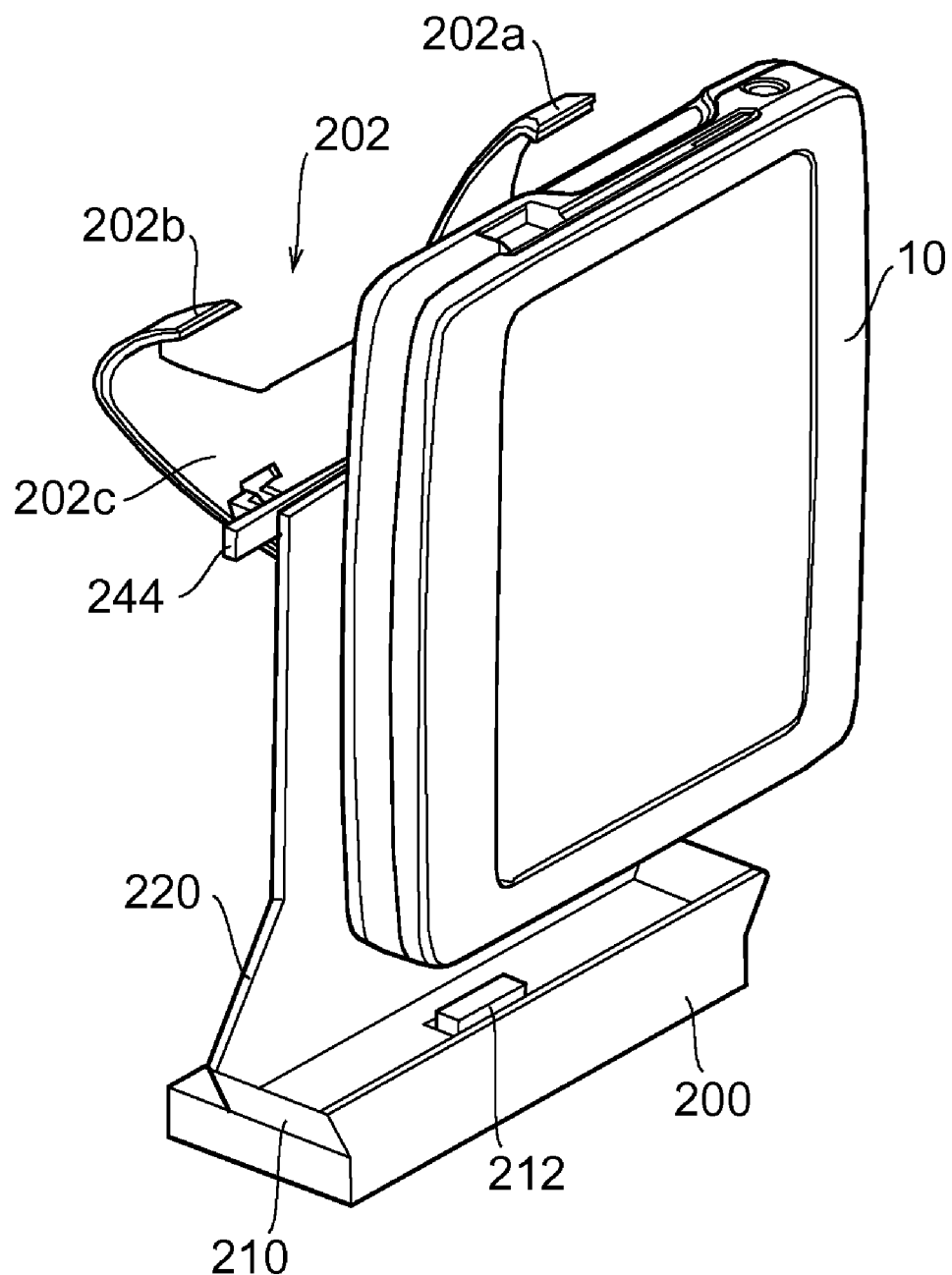
FIG. 3 illustrates in what state the ultrasonic diagnostic device is removed from the docking assembly.

FIG. 3 illustrates in what state the ultrasonic diagnostic device 10 is removed from the docking assembly 200. As shown in FIG. 3, the hold-down member 202 pivots backward at the release position so that the curved portions 202a and 202b do not obstruct removal of the ultrasonic diagnostic device 10.

Now, the ultrasonic diagnostic device 10 can be removed from the docking assembly 200. Upon removal of the ultrasonic diagnostic device 10, the bottom of the device 10 leaves the receptacle section 210 and an electric connection thereof with the receptacle section 210 through a connector 212 is also broken.

A pivotal motion of the hold-down member 202 is performed about a shaft fixed to an end of a flat plate portion 202c that extends from base portions of the curved portions 202a and 202b. The curved portions 202a and 202b are an example of the curved portion in the invention. The flat plate portion 202c is an example of the flat plate portion in the invention.

Figure 4:
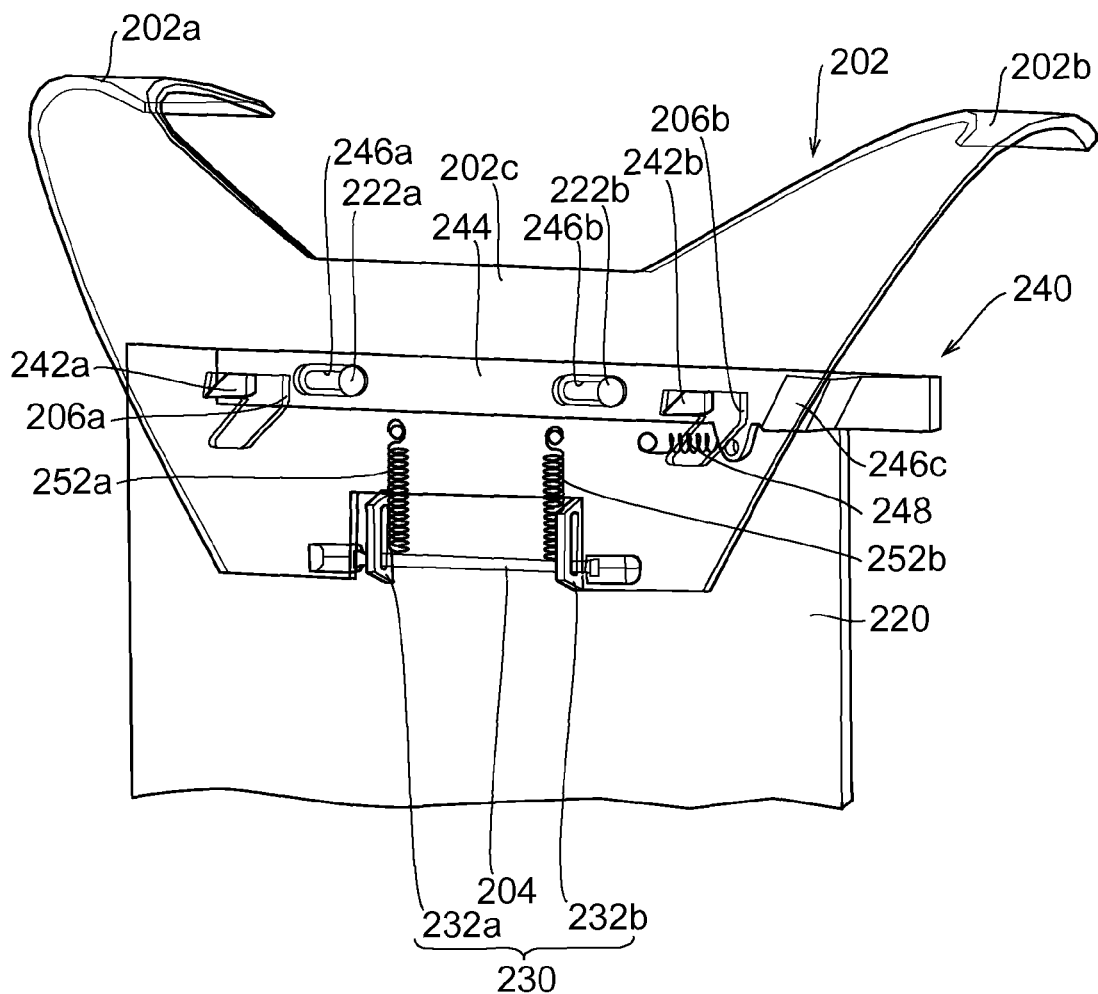
FIG. 4 illustrates the constructions of a hold-down member, a support mechanism and a locking mechanism.

FIG. 4 illustrates the constructions of the hold-down member, support mechanism and locking mechanism as seen from behind the back plate 220. In FIG. 4, the hold-down portion 202 is made transparent so that the portion shaded by the hold-down member 202 can be seen easily.

As shown in FIG. 4, the hold-down member 202 has a shaft 204. The shaft 204 is fixed to a lower end of the flat plate portion 202c that extends downward from the base portions of the curved portions 202a and 202b of the hold-down member 202. The shaft 204 is perpendicular to the extending direction of the flat plate portion 202c and is parallel to the plate surface. The shaft 204 is an example of the shaft in the invention.

A pair of cam slots 206a and 206b are formed in left and right positions of the flat plate portion 202c. The cam slots 206a and 206b are the same in shape and size and are each constituted by a combination of a horizontal slot portion and an oblique slot portion both being continuous with each other at an acute angle. The oblique slot portion extends in a left downward direction acute-anglewise from the right end of the horizontal slot portion. The cam slots 206a and 206b are an example of the cam slot in the invention.

On the back of the back plate 220 there are provided a support mechanism 230, a locking mechanism 240 and a pair of coil springs 252a and 252b. The support mechanism 230 is an example of the support mechanism in the invention. The locking mechanism 240 is an example of the locking mechanism in the invention. The coil springs 252a and 252b are an example of the urging member in the invention.

With a pair of support members 232a and 232b provided on the back of the back plate 220, the support mechanism supports the shaft 204 of the hold-down member 202 horizontally and vertically movably in parallel along the back plate 220. The support members 232a and 232b are an example of the support member in the invention. The force of the pair of coil springs 252a and 252b is constantly exerted upward on the shaft 204. Consequently, the hold-down member 202 is constantly urged upward.

The locking mechanism 240 includes a slide link 244, the slide link 244 having pins 242a and 242b for engagement with the cam slots 206a and 206b respectively of the hold-down member 202. The slide link 244 is mounted horizontally movably through elongated holes 246a and 246b to studs 222a and 222b that are implanted in the back plate 220. The slide link 244 is urged leftwards constantly with a coil spring 248.

The pins 242a and 242b are an example of the pin in the invention. The slide link 244 is an example of the link in the invention. The coil spring 248 is an example of the urging member in the invention.

A right end portion of the slide link 244 serves as a knob for manual operation. The knob is formed so that the user can hold the knob and slide the slide ink 244 rightwards against the reaction force of the coil spring 248.

A hook-like guard 246c is provided near the knob for manual operation. With a hook portion opposed to the back of the hold-down member 202, the guard 246c guards the hold-down member 202.

When manual operation is not performed, the slide link 244 is urged by the coil spring 248 and assumes its leftmost position and the pins 242a and 242b engage the horizontal slot portions of the cam slots 206a and 206b, respectively. Consequently, an upward displacement of the hold-down member 202 is inhibited and assumes a locked state. In this locked state, the hold-down member 202 is located at its lowest position and the coil springs 252a and 252b are in the most extended state. This state corresponds to the holding-down condition shown in FIG. 2.

Figure 5:
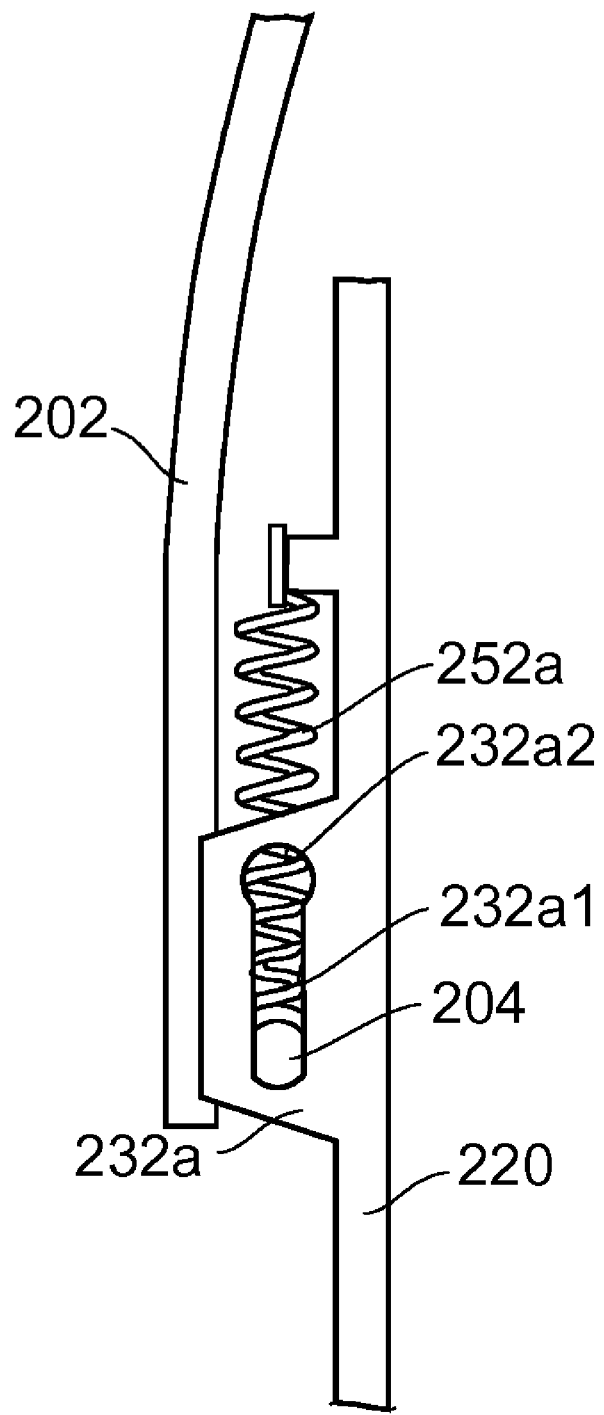
FIG. 5 illustrates the relation between a support member and a shaft in a locked state.

FIG. 5 illustrates on a larger scale the relation between one support member 232a and the shaft 204 in the locked state. The relation between the other support member 232b and the shaft 204 is also the same. As shown in FIG. 5, the support member 232a has a vertically long guide slot 232a1, with the shaft 204 extending through the guide slot 232a1. The shaft 204 has an elliptic sectional shape and the width of the guide slot 232a1 is in conformity with the minor diameter of the ellipse. Consequently, the shaft 204 does not rotate, but can only move in parallel along the guide slot 232a1. As a result, the upright state of the hold-down member 202 is maintained. The guide slot 232a1 is an example of the guide slot in the invention.

A bearing hole 232a2 is formed in an upper end of the guide slot 232a1. The bearing hole 232a2 has an inside diameter conforming to the major diameter of the elliptic section of the shaft 204. Therefore, the shaft 204 is rotatable at the upper end of the guide slot 232a1. The bearing hole 232a2 is an example of the bearing hole in the invention.

Figure 6:
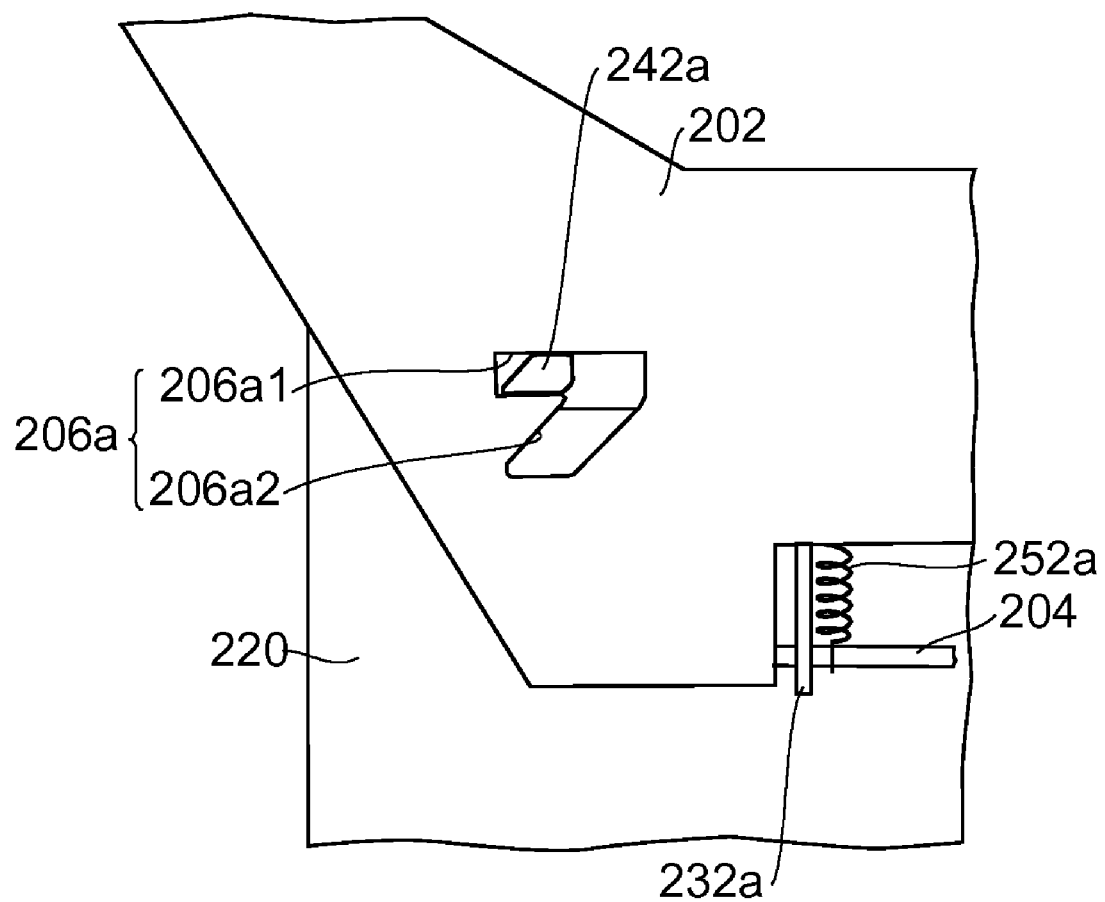
FIG. 6 illustrates the relation between a pin and a cam slot in a locked state.

FIG. 6 illustrates on a larger scale the relation between one pin 242a and the cam slot 206a in the locked state. The relation between the other pin 242b and the cam slot 206b is also the same. As shown in FIG. 6, the underside of the pin 242a is in contact with a horizontal slot portion 206a1 of the cam slot 206a to inhibit an upward movement of the hold-down member 202.

Figure 7:
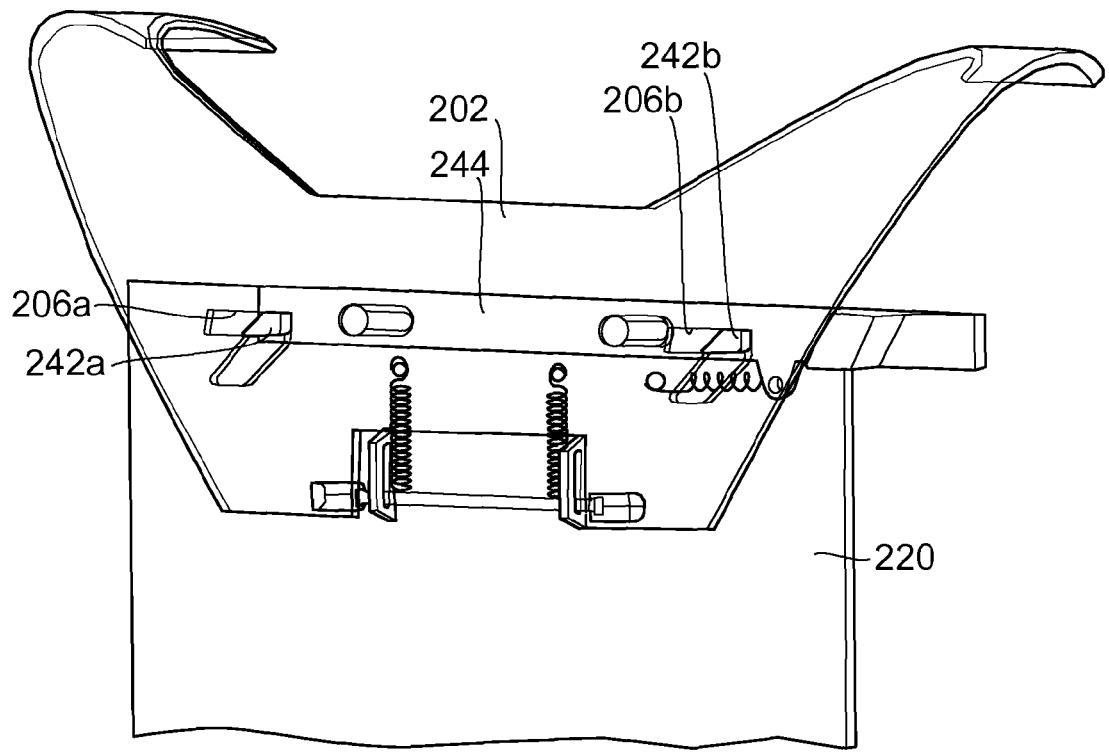
FIG. 7 illustrates a rightwards slid state of a slide link by manual operation.

FIG. 7 illustrates a rightwards slid state of the slide link 244 by manual operation. In this state the pins 242a and 242b are displaced up to the right-end corners of the cam slots 206a and 206b, respectively. The relation between the pin 242a and the cam slot 206a in this state is shown on a larger scale in FIG. 8. The relation between the pin 242b and the cam groove 206b is also the same.

Figure 8:
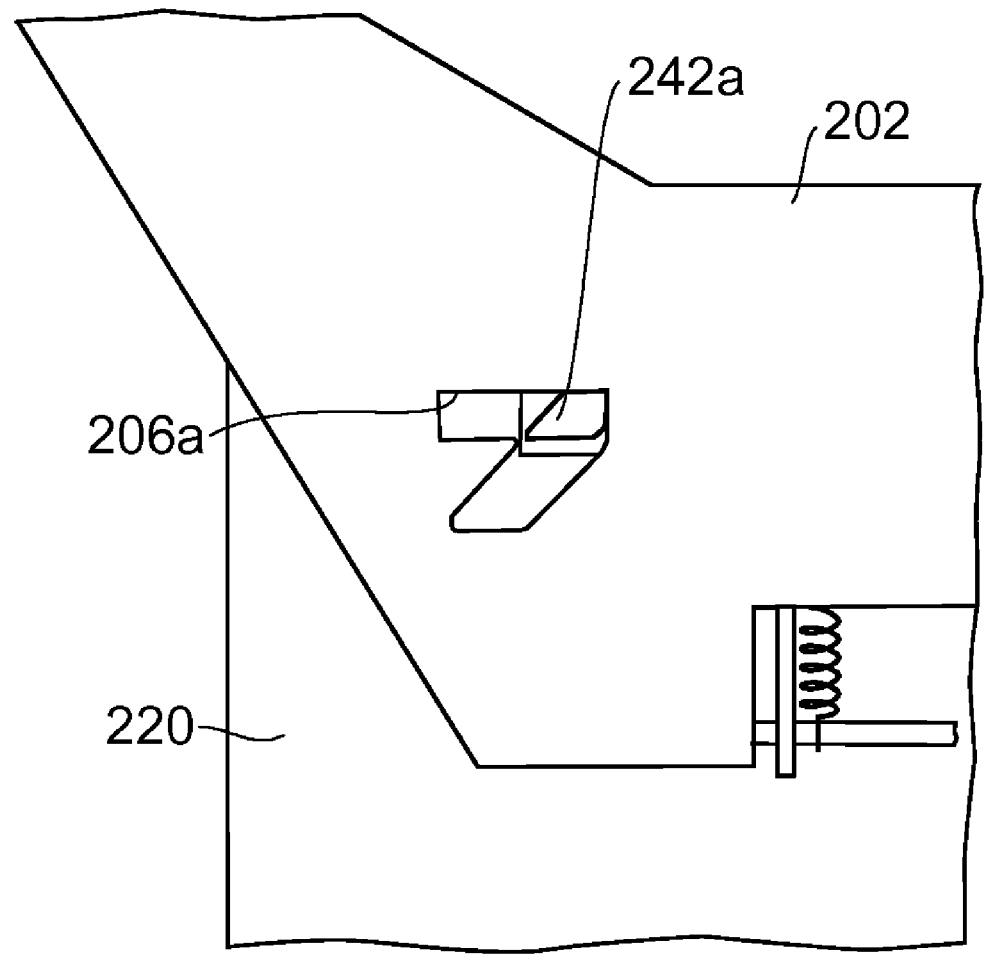
FIG. 8 illustrates the relation between the pin and the cam slot in the rightwards slid state of the slide link by manual operation.
Figure 9:
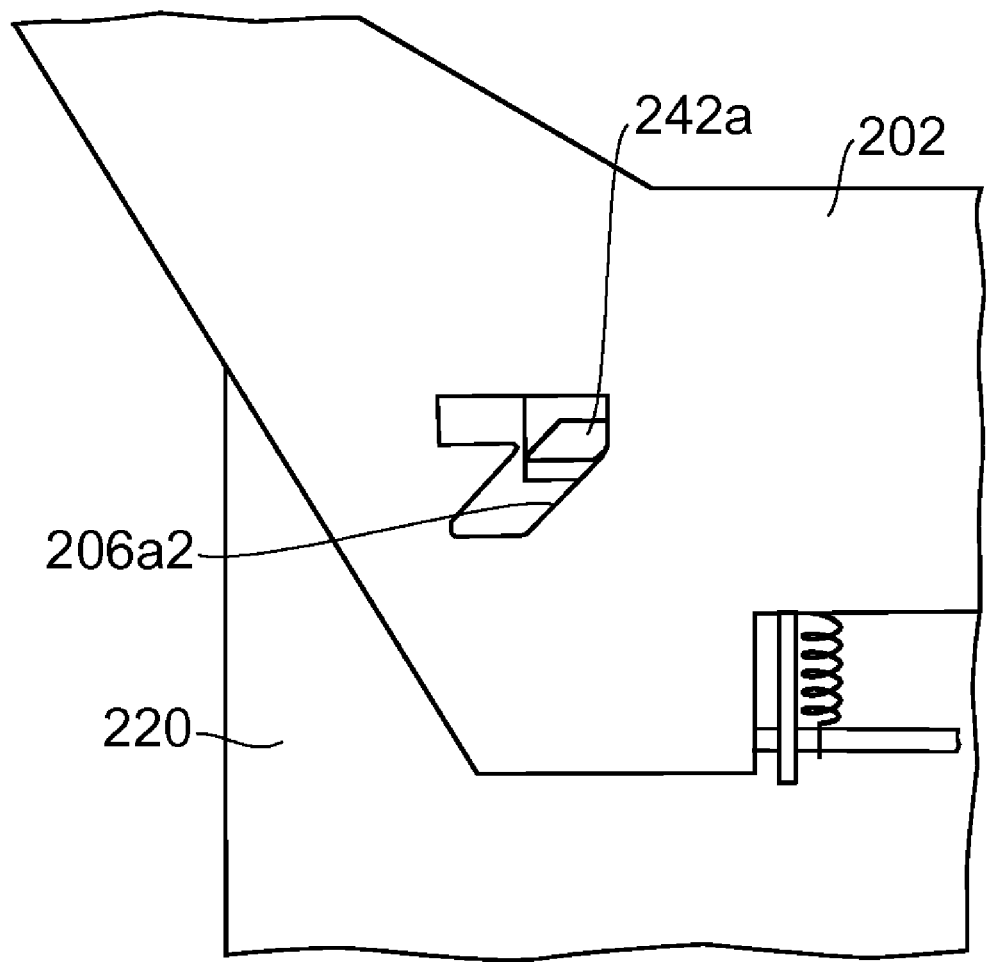
FIG. 9 illustrates a state of contact between an oblique slot portion and the pin.

As shown in FIG. 8, as a result of displacement of the pin 242a up to the right-end corner of the cam slot 206a, the underside of the pin 242a is no longer in contact with the horizontal slot portion 206a1. Consequently, the locked state is released and the hold-down member 202 rises, so that an oblique slot portion 206a2 comes into contact with the pin 242a, as shown in FIG. 9.

Figure 10:
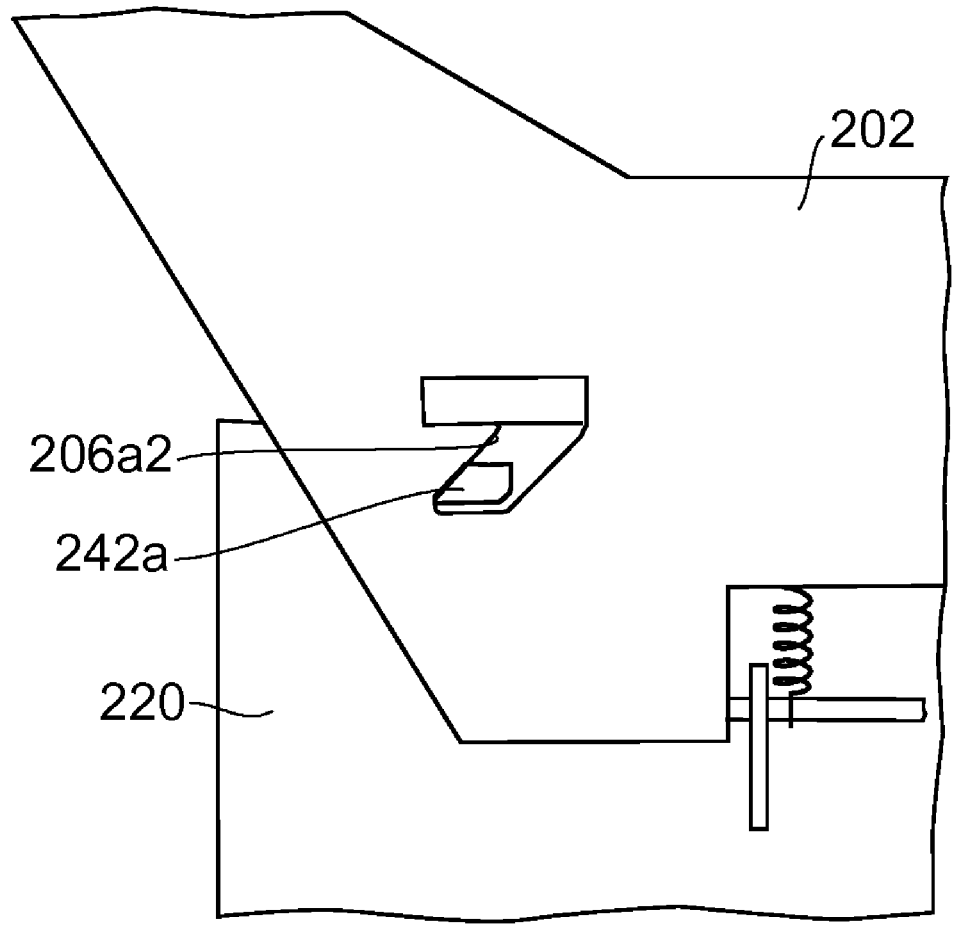
FIG. 10 illustrates a state of contact between the oblique slot portion and the pin.

If the user releases the hold of the slide link 244, the slide link 244 returns leftwards and the hold-down member 202 rises, so that the pin 242a moves left and downward along the oblique slot portion 206a2 and stops at a lower end of the oblique slot portion 206a2, as shown in FIG. 10. At the same time, the rising of the hold-down member 202 also stops.

Figure 11:
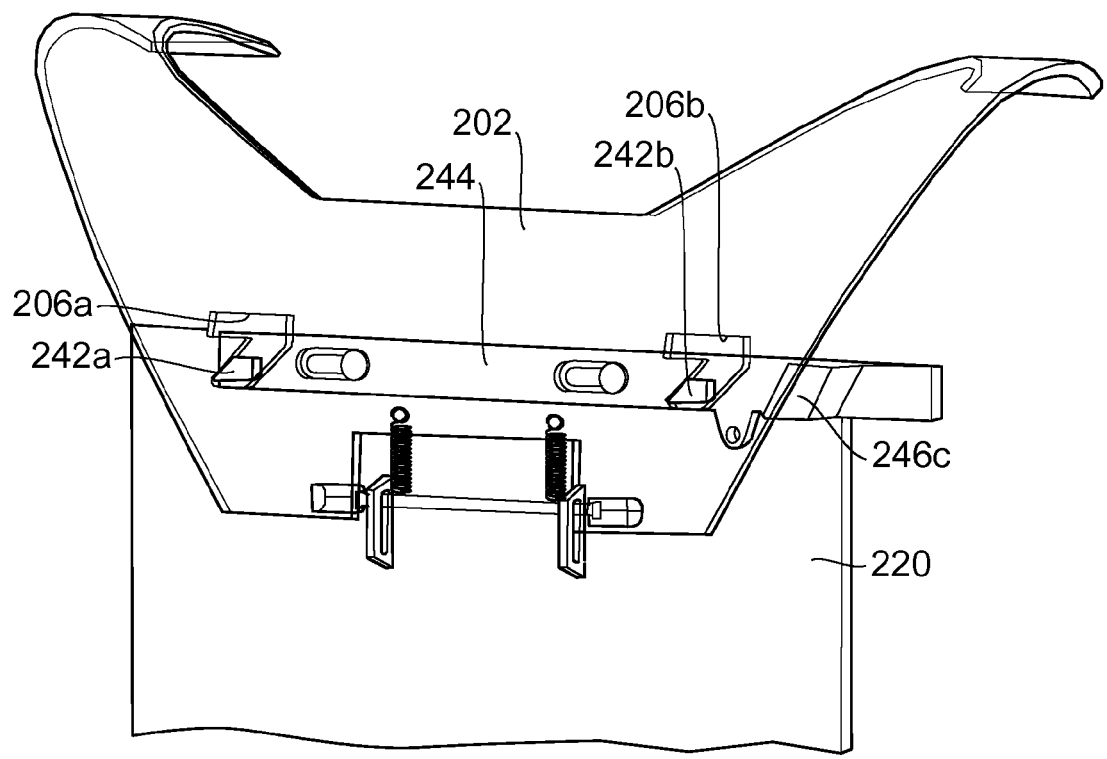
FIG. 11 illustrates a stopped state at a risen position of the hold-down member.

FIG. 11 illustrates a stopped state at the risen position of the hold-down member 202. As shown in FIG. 11, the hold-down member 202 rises until arrival of the shaft 204 at the upper ends of the guide slots of the support members 232a and 232b, then stops. At this position the hold-down member 202 is outside the guard range of the guard 246c.

Figure 12:
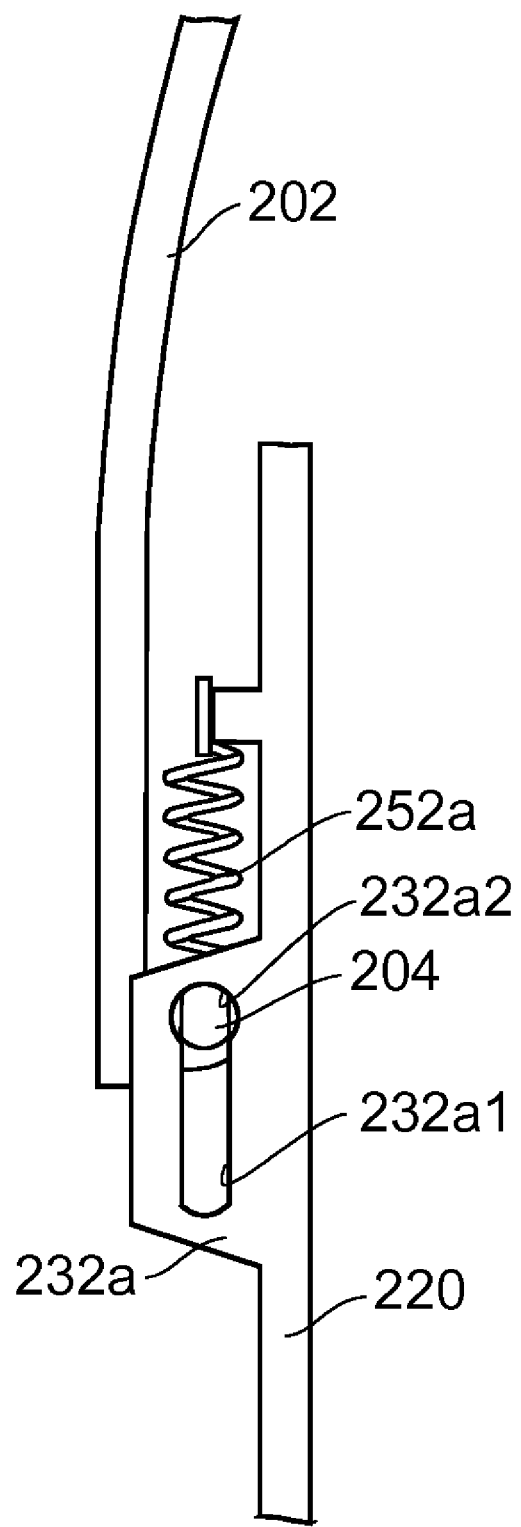
FIG. 12 illustrates the relation between the support member and the shaft in the stopped state at the risen position of the hold-down member.
Figure 13:
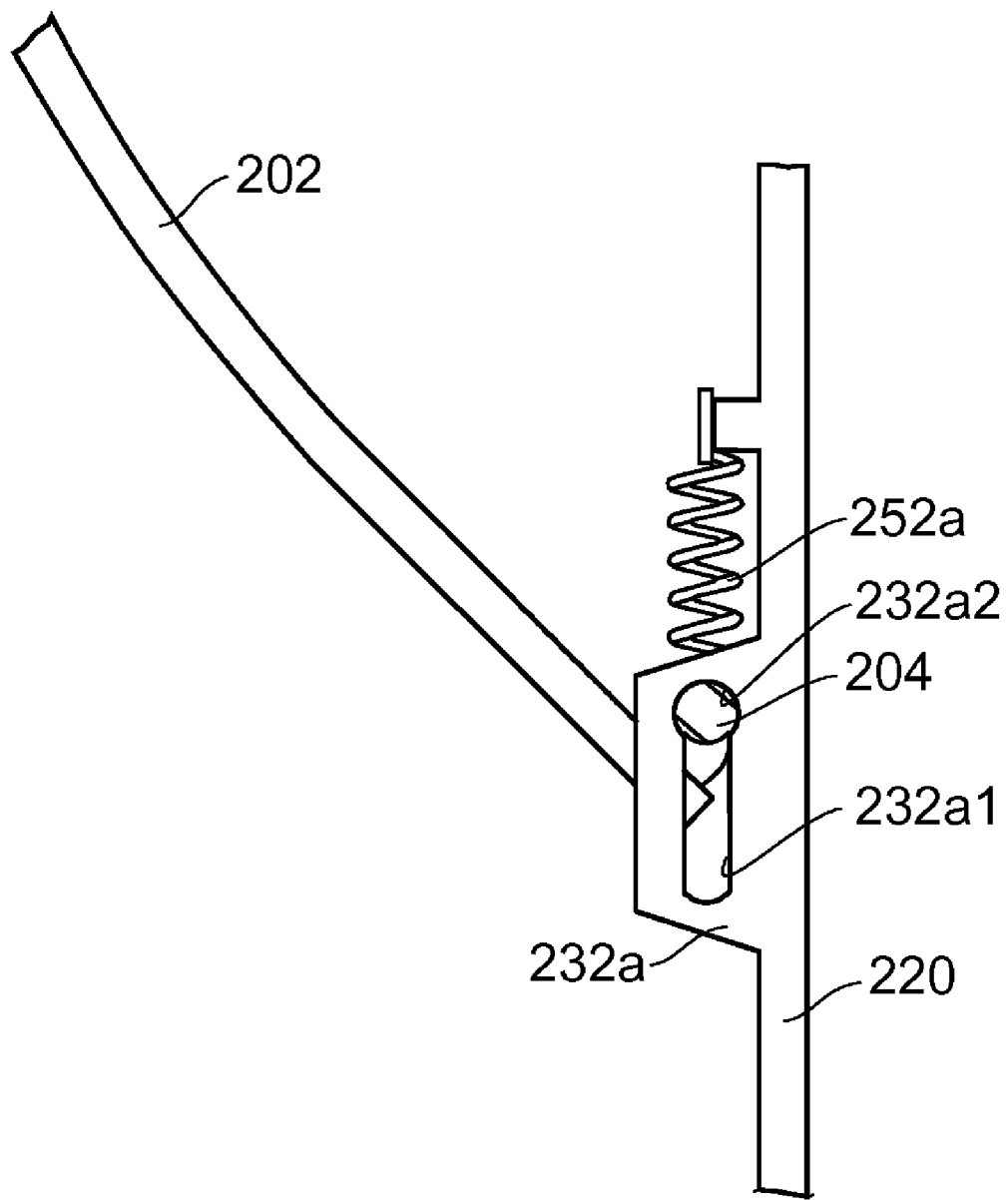
FIG. 13 illustrates a pivoted state of the hold-down member.

FIG. 12 illustrates on a larger scale the relation between one support member 232a and the shaft 204 in a stopped state at the risen position. The relation between the other support member 232b and the shaft 204 is also the same. As shown in FIG. 12, the shaft 204 reaches the upper end of the guide slot 232a1 and is supported by the bearing hole 232a2. Consequently, as shown in FIG. 13, the hold-down member 202 can pivot about the shaft 204.

Figure 14:
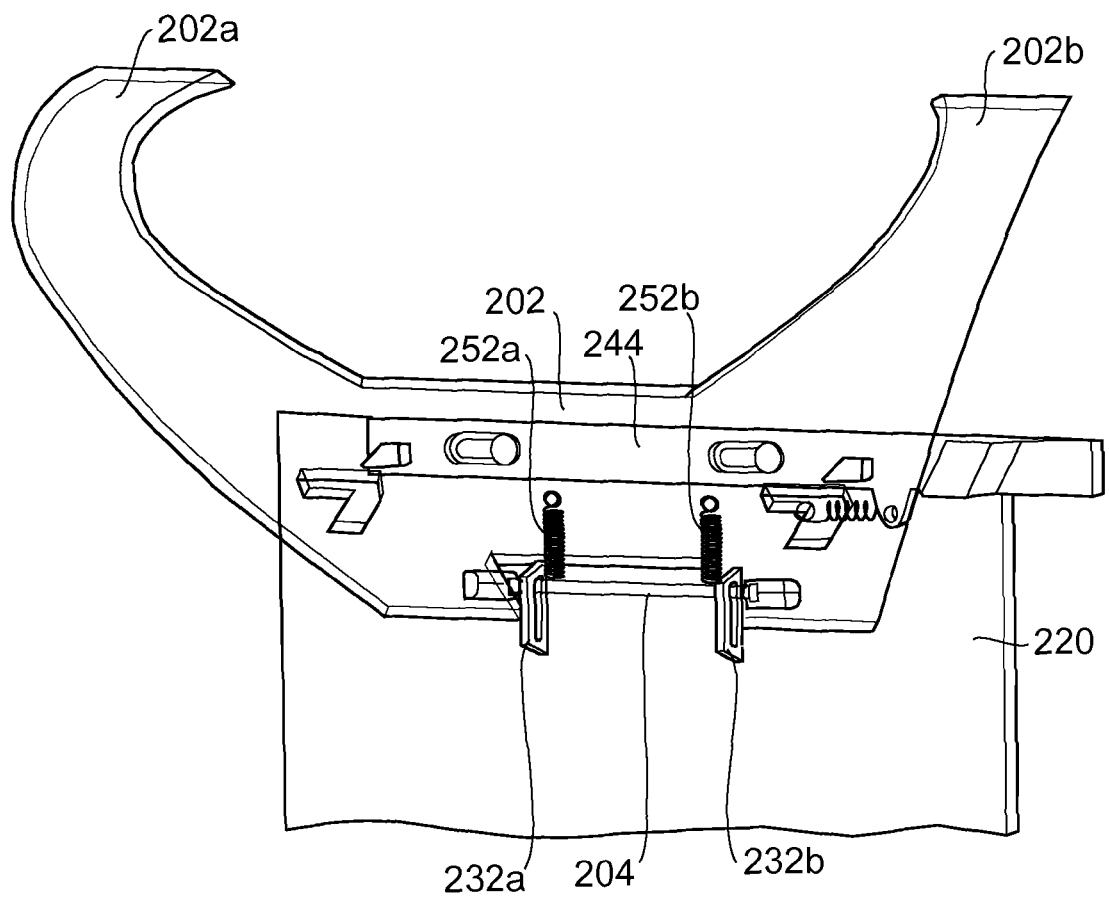
FIG. 14 illustrates a pivoted state of the hold-down member.

FIG. 14 illustrates a pivoted state of the hold-down member 202. The pivoting of the hold-down member 202 is performed manually. As shown in FIG. 14, the hold-down member 202 pivots backward and the curved portions 202a and 202b retracts from the upper space of the back plate 220. This state corresponds to the released state shown in FIG. 3.

When the hold-down member 202 is raised upright in the state of FIG. 14, a return is made to the state of FIG. 11. When the hold-down member 202 is pushed in downwards in the state of FIG. 11, the pins 242a and 242b rise along the oblique slot portions of the cam slots 206a and 206b, respectively, until arriving at the right-end corners, whereupon the pins move up to the left ends. In this way a return is made to the state of FIG. 4.

As described above, by only unlocking with manual operation of the slide link 244, the hold-down member 202 rises itself up to the release position and becomes pivotable at the same position. Thus, the removal of the ultrasonic diagnostic device 10 can be done by such an extremely simple operation.

The mounting of the ultrasonic diagnostic device 10 can also be done by a simple operation because it is completed by only installing the ultrasonic diagnostic device 10 in an upright state on the receptacle section 210 of the docking assembly 200 and raising the hold-down member 202 upright and pushing it downwards.

Many widely different embodiments of the invention may be configured without departing from the spirit and the scope of the present invention. It should be understood that the present invention is not limited to the specific embodiments described in the specification, except as defined in the appended claims.

What is claimed is:

1. A docking station to which a tablet type electronic device is able to be removably mounted, the docking station comprising:
   a receptacle section against which a first side of the electronic device comes into abutment when mounting the electronic device; and
   a hold-down section configured to releasably hold down the electronic device on a second side of the electronic device opposite to the first side when mounting the electronic device, wherein said hold-down section comprises:
      a hold-down member configured to hold down the second side of the electronic device when the electronic device is mounted to the docking station, wherein said hold-down member comprises:
         a curved portion adapted to cover the second side of the electronic device when holding down the electronic device;
         a flat plate portion extending from a base portion of said curved portion;
         a cam slot formed in said flat plate portion; and
         a shaft of an elliptic section provided at an end in an extending direction of said flat plate portion perpendicularly to the extending direction and in parallel with said plate surface; and
      a support mechanism configured to support said hold-down member such that said hold-down member is movable between a hold-down position and a release position and pivotable in a direction away from the electronic device at the release position, when the electronic device is mounted to the docking station, wherein said support mechanism comprises:
         a support member configured to support said shaft of said hold-down member such that said shaft is movable in parallel between the hold-down position and the release position and rotatable at the release position, wherein said support member comprises:
            a guide slot having a width conforming to a minor diameter of said elliptic section of said shaft and also having a length corresponding to a distance between the hold-down position and the release position; and
            a bearing hole formed in an end of a release position side of said guide slot and having an inside diameter conforming to a major diameter of said elliptic section of said shaft.

2. A docking station according to claim 1, wherein said hold-down section further comprises:

a locking mechanism configured to releasably lock said hold-down member at the hold-down position when the electronic device is mounted to the docking station; and an urging member configured to urge said hold-down member from the hold-down position toward the release position.

3. A docking station according to claim 2, wherein said locking mechanism comprises:

a pin adapted to engage said cam slot of said hold-down member to lock said hold-down member in the hold-down position;

a link adapted to be operated manually to cause said pin to move along said cam slot, thereby releasing said hold-down member locked by said pin; and an urging member configured to urge said link in a direction opposite to a direction of the manual operation.

4. A docking station according to claim 2, wherein said urging member comprises a coil spring.

5. A docking station according to claim 1, wherein said hold-down section is configured to hold down the electronic device in a direction to push the electronic device against said receptacle section when the electronic device is mounted to the docking station.

6. A docking station according to claim 1, wherein said receptacle section comprises an electrical connector.

7. A docking station according to claim 1, wherein said receptacle section is configured to receive therein the electronic device which is in an upright state with respect to the docking station.

8. An ultrasonic diagnostic system comprising:

a tablet type electronic device configured for use in ultrasonic diagnosis; and a docking station which is removably connected with said electronic device, said docking station comprising:

a receptacle section against which a first side of said electronic device comes into abutment when mounting said electronic device; and a hold-down section configured to releasably hold down said electronic device on a second side of the electronic device opposite to the first side when mounting said electronic device, wherein said hold-down section comprises:

a hold-down member configured to hold down the second side of said electronic device, wherein said hold down member comprises:

a curved portion adapted to cover the second side of said electronic device when holding down said electronic device;

a flat plate portion extending from a base portion of said curved portion;

a cam slot formed in said flat plate portion; and a shaft of an elliptic section provided at an end in an extending direction of said flat plate portion perpendicularly to the extending direction and in parallel with said plate surface; and a support mechanism configured to support said hold-down member such that said hold-down member is movable between a hold-down position and a release position and pivotable in a direction away from said electronic device at the release position, wherein said support mechanism comprises:

a support member configured to support said shaft of said hold-down member such that said shaft is movable in parallel between the hold-down position and the release position and rotatable at the release position, wherein said support member comprises:

a guide slot having a width conforming to a minor diameter of said elliptic section of said shaft and also having a length corresponding to a distance between the hold-down position and the release position; and a bearing hole formed in an end of a release position side of said guide slot and having an inside diameter conforming to a major diameter of said elliptic section of said shaft.

9. An ultrasonic diagnostic system according to claim 8, wherein said hold-down section further comprises:

a locking mechanism configured to releasably lock said hold-down member at the hold-down position; and an urging member configured to urge said hold-down member from the hold-down position toward the release position.

10. An ultrasonic diagnostic system according to claim 9, wherein said locking mechanism comprises:

a pin adapted to engage said cam slot of said hold-down member to lock said hold-down member in the hold-down position;

a link adapted to be operated manually to cause said pin to move along said cam slot, thereby releasing said hold-down member locked by said pin; and an urging member configured to urge said link in a direction opposite to a direction of the manual operation.

11. An ultrasonic diagnostic system according to claim 9, wherein said urging member comprises a coil spring.

12. An ultrasonic diagnostic system according to claim 8, wherein said hold-down section is configured to hold down said electronic device in a direction to push said electronic device against said receptacle section.

13. An ultrasonic diagnostic system according to claim 8, wherein said receptacle section comprises an electrical connector.

14. An ultrasonic diagnostic system according to claim 8, wherein said receptacle section is configured to receive therein said electronic device which is in an upright state with respect to said docking station.

* * * * *